(12) United States Patent
Aoki et al.

(10) Patent No.: US 6,358,494 B1
(45) Date of Patent: Mar. 19, 2002

(54) COMPOSITE TOOTHPASTE PRODUCTS

(75) Inventors: Hideki Aoki, Inashiki-gun; Marehito Aoki; Hidenao Aoki, both of Tokyo, all of (JP)

(73) Assignee: Tokyo Bioceramics Institute Co., Ltd., Tokyo (JP)

( * ) Notice: Subject to any disclaimer, the term of this patent is extended or adjusted under 35 U.S.C. 154(b) by 0 days.

(21) Appl. No.: 09/381,950

(22) PCT Filed: Mar. 26, 1998

(86) PCT No.: PCT/JP98/01343

§ 371 Date: Dec. 1, 1999

§ 102(e) Date: Dec. 1, 1999

(87) PCT Pub. No.: WO98/42299

PCT Pub. Date: Oct. 1, 1998

(30) Foreign Application Priority Data

Mar. 26, 1997 (JP) .............................. 9-092940

(51) Int. Cl.[7] .............................. A61K 7/18; A61K 7/16
(52) U.S. Cl. .............................. 424/52; 222/94; 424/49; 424/57
(58) Field of Search .................. 424/49–58; 222/94

(56) References Cited

U.S. PATENT DOCUMENTS

| | | | | |
|---|---|---|---|---|
| 1,676,734 A | * | 7/1928 | Hopkins | |
| 1,825,865 A | * | 10/1931 | Hopkins | |
| 3,335,912 A | * | 8/1967 | Reeves | 222/94 |
| 3,747,804 A | * | 7/1973 | Raaf et al. | 222/1 |
| 3,980,222 A | * | 9/1976 | Hood | 229/22 |
| 4,098,435 A | * | 7/1978 | Weyn | 229/94 |
| 4,211,341 A | * | 7/1980 | Weyn | 222/94 |
| 4,327,079 A | * | 4/1982 | Aoki | 424/57 |
| 4,342,741 A | * | 8/1982 | Anki | 424/57 |
| 4,634,589 A | * | 1/1987 | Schellor | 424/49 |
| 4,988,499 A | * | 1/1991 | Bristow et al. | 424/52 |
| 5,089,254 A | * | 2/1992 | Coulson | 424/52 |
| 5,112,599 A | * | 5/1992 | Coulson | 424/52 |
| 5,244,120 A | * | 9/1993 | O'Meara | 222/94 |
| 5,269,441 A | * | 12/1993 | O'Meara | 222/94 |
| 5,318,203 A | * | 6/1994 | Iaia et al. | 222/94 |
| 5,603,922 A | * | 2/1997 | Winston et al. | 424/49 |
| 5,605,675 A | * | 2/1997 | Usen et al. | 424/49 |
| 5,628,429 A | * | 5/1997 | Usen et al. | 222/1 |
| 5,860,565 A | * | 1/1999 | Winston et al. | 222/1 |
| 5,895,641 A | * | 4/1999 | Usen et al. | 424/52 |
| 6,129,243 A | * | 10/2000 | Pal et al. | 222/94 |
| 6,159,448 A | * | 12/2000 | Winston et al. | 424/52 |
| 6,159,449 A | * | 12/2000 | Winston et al. | 424/52 |

* cited by examiner

Primary Examiner—Shep K. Rose
(74) Attorney, Agent, or Firm—Reed Smith LLP

(57) ABSTRACT

A composite toothpaste product comprising a toothpaste containing a hydroxyapatite as a main active ingredient and another toothpaste containing a fluorine compound as a main active ingredient, which are enclosed with a container made of, for instance, a flexible tube but separated from each other by a partition united to the container. In the composite toothpaste product, the toothpastes are separated from each other with no contact when it is out of use, and are squeezed out of the container, when in use, in such a manner that the latter toothpaste is enclosed with the former. It is far more effective in removing bacterial plaque, improving tooth whiteness, and preventing dental caries than the conventional toothpaste products containing only either a hydroxyapatite or a fluorine compound.

5 Claims, 1 Drawing Sheet

COMPOSITE TOOTHPASTE PRODUCTS

FIELD OF THE INVENTION

The present invention relates to a composite toothpaste product containing a fluorine compound and a hydroxyapatite in combination. In particular, the invention relates to an improved composite toothpaste product which imparts favorable effects to teeth by way of the activity of the fluorine compound as well as the activity of the hydroxyapatite, when the teeth are brushed.

BACKGROUND OF THE INVENTION

The toothpaste generally comprises water, a wetting agent, and an abrasive. Until now, proposals to incorporate a variety of additives into the toothpaste for improving functions of the toothpaste have been made. Some of these proposals have been employed in the production of commercially available toothpastes.

A representative additive is a fluorine compound. It has been confirmed that a fluorine compound is dissociated in an aqueous toothpaste to give a fluorine ion which reacts with a surface layer of the tooth to enhance the surface hardness of the tooth. A toothpaste containing a fluorine compound is described in Japanese Patent Provisional Publication No. 46-4150.

Recently, incorporation of a hydroxyapatite having the same chemical composition as that of the tooth into a toothpaste has been studied. The incorporation of a hydroxyapatite is described in Japanese Patent Provisional Publications No. 55-57514, No. 56-73014, No. 56-73015, No. 60-206678, No. 61-91333, and No. 57-185213. Since the hydroxyapatite has the same chemical composition as that of tooth, it has a high affinity to the tooth and can be attached to a defective portion of tooth produced by dental caries when it is incorporated into a toothpaste. Further, the hydroxyapatite is effective for removing a bacterial plaque attached to the tooth. For these reasons, a toothpaste containing a hydroxyapatite is commercially available.

As described above, each of a fluorine compound and a hydroxyapatite imparts to a toothpaste an additional performance. Therefore, it has been studied to incorporate both chemicals in combination into toothpastes. It has been noted, however, that a fluorine compound is highly reactive to a hydroxyapatite and the incorporation both chemicals into a toothpaste causes a reaction between them to produce a fluorinated apatite or a calcium fluoride which is very hard. Accordingly, the performances of the both chemicals cannot be utilized in the toothpaste.

Japanese Patent Provisional Publication No. 58-219107 proposes to prepare a fluorine ion source and a calcium ion source (no hydroxyapatite is mentioned) separately and to utilize them sequentially or simultaneously when teeth are brushed.

Japanese Patent Provisional Publication No. H1-6213 (which corresponds to Japanese Patent Publication (examined) No. H2-31049) discloses a toothpaste which comprises microcapsules containing a hydroxyapatite (or a fluorine compound) and a supporting material containing a fluorine compound (or a hydroxyapatite) in which the microcapsules are dispersed.

The present inventors studied these known composite toothpaste products and noted that these products hardly give to the toothpastes the target combined effects. In more detail, the composite toothpaste product of Japanese Patent Provisional Publication No. 58-219107 requires two toothpastes which should be encased in different vessels and which are necessarily employed in combination when teeth are brushed. In the microcapsuled toothpaste of Japanese Provisional Publication H1-6213, the wall of the microcapsule is sometimes not enough for reliably separating the fluorine compound from the hydroxyapatite, and therefore the reaction between both chemicals possibly proceeds during storage of the toothpaste product. If the wall of the microcapsule has an increased thickness, the reaction is effectively obviated. In that case, however, the microcapsules are hardly broken in the brushing procedure and the performance of the microcapsuled chemical is hardly utilized.

Further studies by the present inventors have revealed that when a fluorine compound and a hydroxyapatite are simultaneously employed in the teeth brushing procedure and the fluorine compound is first brought into contact with teeth, the teeth rapidly react with the fluorine compound to form a hard surface layer thereon and hence the desired contact of the hydroxyapatite to the teeth is disturbed. Moreover, it has been noted that a fluorine compound is preferably brought into contact with teeth after the teeth are covered with a hydroxyapatite so that the effect of hardening tooth surface to be provided by a fluorine compound can not be attained.

SUMMARY OF THE INVENTION

The present invention resides in a composite toothpaste product comprising a toothpaste containing a hydroxyapatite as a main active ingredient and another toothpaste containing a fluorine compound as a main active ingredient, which are enclosed with a container but separated from each other by a partition united to the container, under the condition that these toothpastes are separated from each other with no contact when it is out of use, and are squeezed out of the container, when in use, in such a manner that the latter toothpaste is enclosed with the former toothpaste.

The above-mentioned composite toothpaste product of the invention preferably has such a structure that the container comprises double tubes in which one is an outer flexible tube having one open end and another is an inner flexible tube having one open end, the open end of the inner tube being put back from the position of the open end of the outer tube in the longitudinal direction of the tubes, the toothpaste containing a fluorine compound being placed in the inner tube, and the toothpaste containing a hydroxyapatite being placed in a space formed between the inner tube and the outer tube.

In the invention, the hydroxyapatite is preferably contained in the toothpaste containing an hydroxyapatite in an amount of 1 to 30 weight %, based on the total amount of the toothpaste containing an hydroxyapatite and the toothpaste containing a fluorine compound, and the fluorine compound is preferably contained in the toothpaste containing a fluorine compound in an amount of 0.002 to 2.0 weight % in terms of an amount of fluorine ion, based on the total amount of the toothpaste containing an hydroxyapatite and the toothpaste containing a fluorine compound. It is also preferred that the fluorine compound is contained in the toothpaste containing a fluorine compound in an amount of 0.001 to 3.0 weight % in terms of an amount of fluorine ion, based on the amount of the hydroxyapatite contained in the toothpaste containing an hydroxyapatite.

DETAILED DESCRIPTION OF THE INVENTION

The composite toothpaste product of the invention is further described by referring to the attached drawings.

Figure 1:
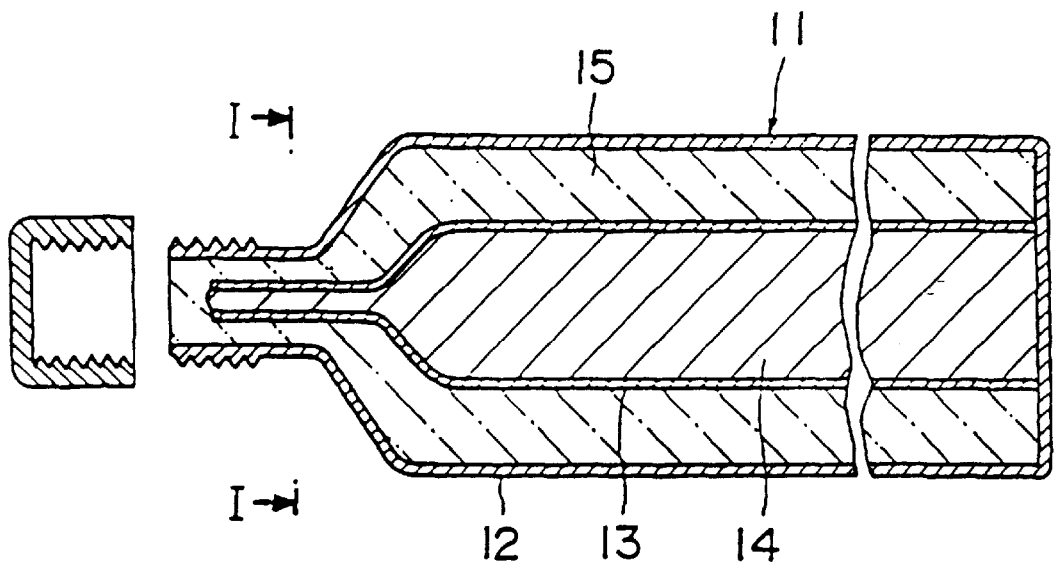
FIG. 1 is a schematic section of a representative composite toothpaste product according to the invention.
Figure 2:
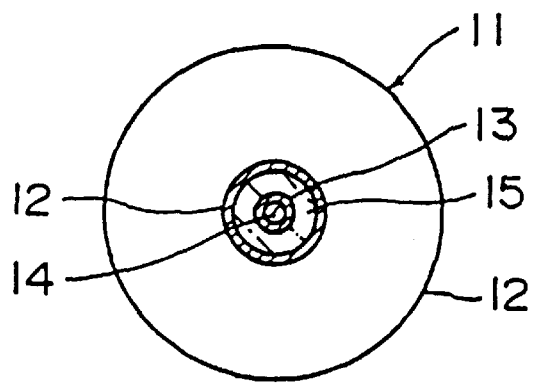
FIG. 2 is a section of the toothpaste product of FIG. 1, taken along I—I line.

FIG. 1 is a schematic view of a section indicating a representative structure of the composite toothpaste product of the invention which utilizes a cylindrical double tube 11 made of flexible material. FIG. 2 is a section of the toothpaste product of FIG. 1, taken along I—I line. The cylindrical double tube 11 comprises an outer tube 12 and a coaxially arranged inner tube 13, both of which are made of a flexible sheet such as a metal sheet. The open end (for pushing out one toothpaste) of the inner tube 13 is put back from the open end (for pushing out another toothpaste) of the outer tube 12. In the inner tube 13, a fluorine toothpaste 14 (i.e., a toothpaste containing a fluorine compound) is contained. Between the inner tube 13 and the outer tube 12, a hydroxyapatite toothpaste 15 (i.e., a toothpaste containing a hydroxyapatite) is placed.

In carrying out tooth-brushing, a pressure is applied to the side surfaces of the toothpaste product of the invention in the conventional manner. The outer hydroxyapatite toothpaste 15 is first pushed out, and subsequently the inner fluorine toothpaste 14 is pushed out in such a manner that the fluorine toothpaste is enclosed with the hydroxyapatite toothpaste. When the pressure is removed, the pushed-out toothpastes are separated from the tubes under the condition that the end of the pushed-out fluorine toothpaste 14 is also enclosed with the pushed-put hydroxyapatite toothpaste 15, as is schematically illustrated in FIG. 3.

Figure 3:
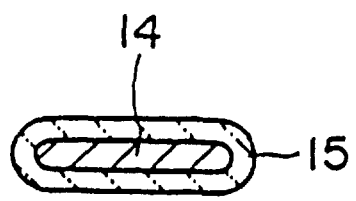
FIG. 3 schematically illustrates a section of a toothpaste having been pushed out of the container.

The combined toothpastes illustrated in FIG. 3 are placed on a toothbrush, and brought into contact with teeth. Accordingly, the hydroxyapatite toothpaste 15 is first brought into contact with teeth, and the fluorine toothpaste 14 is subsequently brought into contact with teeth which are already treated with the hydroxyapatite toothpaste. Therefore, the functions of the hydroxyapatite, that is, plugging defective tooth portions and removing bacterial plaque, are effectively realized, and then the tooth surface which is repaired and coated by hydroxyapatite is hardened by action of a fluorine ion.

The composition of the composite toothpaste product of the invention is described below in more detail.

The fluorine toothpaste contains as an active ingredient a fluorine compound which releases a fluorine ion in water. The fluorine compound can be sodium monofluorophosphate which is generally employed in tooth pastes. However, a fluorine compound having a higher activity, such as sodium fluoride, is preferably employed in the invention. A fluorine compound having such a high activity is apt to cause troubles during storage of toothpastes containing such fluorine compound and in the tooth brushing procedure.

In contrast, the composite toothpaste product of the invention comprises a fluorine-containing toothpaste and a hydroxyapatite-containing toothpaste which are well separated from each other. In the tooth-brushing procedure, the hydroxyapatite-containing toothpaste is first brought into contact with teeth for pre-treatment.

Therefore, the highly active fluorine compound is stably stored and functions safely in the tooth-brushing procedure.

A variety of compositions are known for formulating fluorine-containing toothpastes. Further known are various additional ingredients and additives as well as amounts of these chemicals. These known chemicals and technology are utilizable for formulating the fluorine-containing containing toothpaste to be employed in the invention.

Also known is a hydroxyapatite for incorporation into toothpastes. A variety of compositions are also known for formulating hydroxyapatite-containing toothpastes. Further known are various additional ingredients and additives as well as amounts of these chemicals. These known chemicals and technology are utilizable for formulating the hydroxyapatite-containing toothpaste to be employed in the invention. The hydroxyapatite preferably has a particle size (a size of a primary particle) of not more than 5.0 μm, more preferably in the range of 0.01 to 1.0 μm. The specific surface area preferably is in the range of 10 to 100 $m^2/g$.

There are no specific limitations with respect to material to be used for the preparation of the containers of the composite toothpaste product according to the invention. In consideration of the daily tooth-brushing procedure, however, the double tube structure illustrated in FIG. 1 and FIG. 2 is preferred. The containers are also preferred to be produced by a flexible sheet such as a metal film or a laminate of a metal film and a plastic resin film.

EXAMPLE 1

(1) Toothpaste Containing Fluorine Compound as Active Ingredient

| | |
|---|---|
| Aluminum hydroxide | 15 wt. % |
| Silicic acid anhydride | 7 wt. % |
| Alumina | 2 wt. % |
| Glycerol | 15 wt. % |
| Sorbitol | 15 wt. % |
| Carboxymethylcellulose | 2 wt. % |
| Sodium laurylsulfate | 2 wt. % |
| Sodium fluoride | 0.1 wt. % |
| Flavor | 1 wt. % |
| Pure water | 40.9 wt. % |

The above-mentioned ingredients were mixed and kneaded in the conventional manner to prepare a fluorine-containing toothpaste.

(2) Toothpaste Containing Hydroxyapatite as Active Ingredient

| | |
|---|---|
| Hydroxyapatite | 15 wt. % |
| Calcium hydrogen phosphate ($2H_2O$) | 20 wt. % |
| Glycerol | 10 wt. % |
| Sorbitol | 10 wt. % |
| Carboxymethylcellulose | 1 wt. % |
| Sodium laurylsulfate | 2 wt. % |
| Saccharin sodium salt | 0.1 wt. % |
| Flavor | 1 wt. % |
| Pure water | 40.9 wt. % |

The above-mentioned ingredients were mixed and kneaded in the conventional manner to prepare a hydroxyapatite-containing toothpaste.

(3) Composite Toothpaste Tube

The fluorine-containing toothpaste and the hydroxyapatite-containing toothpaste prepared above were placed in a ratio of 1:3 in a double tube vessel illustrated in FIGS. 1 and 2 under the condition that the former was placed in the inner tube and the latter was placed in the space between the inner tube and the outer tube.

(4) Evaluation of Toothpastes for Increase of Whiteness

1) Fifteen adults (including males and females) were divided into three groups in which each group had five adults. The adults in each group daily performed tooth-brushing twice a day (3 minutes for each brushing) for three days using one of the below-mentioned toothpastes.

Group A: the composite toothpaste product prepared in (3) above

Group B: a commercially available hydroxyapatite-containing toothpaste

Group C: a commercially available fluorine compound-containing toothpaste

After the three day-brushing procedures, whiteness of front teeth at the both first positions on the upper jaw was measured by means of a color-difference meter.

2) Results of Evaluation (Increase of Whiteness)

The results of evaluation are set forth in Table 1 in terms of whiteness value, which are shown by a mean value±standard deviation.

TABLE 1

|  | Group A | Group B | Group C |
| --- | --- | --- | --- |
| Before brushing | 52–65 | 51–72 | 49–66 |
| Increase of whiteness | 10 ± 2 | 4 ± 2 | 1 ± 1 |

Remarks: Whiteness of standard white board = 97 ± 1 Whiteness of white paper = 91 ± 1

The results indicate that prominent increase of whiteness is observed when the tooth-brushing is performed using the composite toothpaste product of the invention.

(5) Evaluation of Toothpastes for Removing Bacterial Plaque

1) The same fifteen adults (including males and females) as above were divided into three groups in which each group had five adults. The amount of bacterial plaque attached to teeth of the adults in each group were measured using a dye after a breakfast was taken. Subsequently, the adults performed tooth-brushing using one of the below-mentioned toothpastes.

Group A: the composite toothpaste product prepared in (3) above

Group B: a commercially available hydroxyapatite-containing toothpaste

Group C: a commercially available fluorine compound-containing toothpaste

After the brushing was complete, the amount of bacterial plaque attached to teeth of the adults was measured using a dye in the same manner to give a plaque index which indicated the effect of toothpaste for removing bacterial plaque.

2) Results of Evaluation (Removal of Bacterial Plaque)

The results of evaluation are set forth in Table 2 in terms of plaque index, which are shown by a mean value±standard deviation.

TABLE 2

|  | Group A | Group B | Group C |
| --- | --- | --- | --- |
| Before brushing | 0.57 ± 0.47 | 0.55 ± 0.49 | 0.60 ± 0.51 |
| After brushing | 0.08 ± 0.11 | 0.12 ± 0.10 | 0.15 ± 0.11 |

The results indicate that marked removal of bacterial plaque is observed when the tooth-brushing is performed using the composite toothpaste product of the invention.

(6) Evaluation of Toothpastes for Inhibition of Dental Caries

1) Thirty children of 10 to 12 age (including boys and girls) were divided into three groups in which each group had ten children. The children in each group daily performed tooth-brushing twice a day (morning and night) for six months using one of the below-mentioned toothpastes.

Group A: the composite toothpaste product prepared in (3) above

Group B: a commercially available hydroxyapatite-containing toothpaste

Group C: a commercially available fluorine compound-containing toothpaste

After the six month-brushing procedures, approximately 7 permanent teeth of each child were observed in each group to count a number of teeth newly having dental caries, and NCIR (new caries incidence rate) was calculated.

2) Results of Evaluation (Inhibition of Dental Caries)

The results of evaluation are set forth in Table 3 in terms of number of teeth having new dental caries and NCIR value.

TABLE 3

|  | Group A | Group B | Group C |
| --- | --- | --- | --- |
| Number of teeth having new dental caries | 2/73 | 4/71 | 6/76 |
| NCIR | 2.7% | 5.6% | 7.9% |

The results indicate that marked effect for inhibition of dental caries is observed when the tooth-brushing is performed using the composite toothpaste product of the invention.

EXAMPLE 2

1) Toothpaste Containing Fluorine Compound as Active Ingredient

| Aluminum hydroxide | 10 wt. % |
| --- | --- |
| Silicic acid anhydride | 3 wt. % |
| Alumina | 3 wt. % |
| Silica | 10 wt. % |
| Sodium chloride | 10 wt. % |
| Glycerol | 10 wt. % |
| Sorbitol | 10 wt. % |
| Carboxymethylcellulose | 1 wt. % |
| Sodium laurylsulfate | 2 wt. % |
| Sodium monofluorophosphate | 0.5 wt. % |
| Flavor | 1 wt. % |
| Pure water | 39.5 wt. % |

The above-mentioned ingredients were mixed and kneaded in the conventional manner to prepare a fluorine-containing toothpaste.

(2) Toothpaste Containing Hydroxyapatite as Active Ingredient

| Hydroxyapatite | 3 wt. % |
| --- | --- |
| Calcium hydrogen phosphate (2H$_2$O) | 37 wt. % |
| Glycerol | 10 wt. % |
| Sorbitol | 10 wt. % |
| Carboxymethylcellulose | 1 wt. % |
| Sodium laurylsulfate | 2 wt. % |
| Saccharin sodium salt | 0.5 wt. % |
| Flavor | 1 wt. % |
| Pure water | 35.5 wt. % |

The above-mentioned ingredients were mixed and kneaded in the conventional manner to prepare a hydroxyapatite-containing toothpaste. available toothpastes containing a hydroxyapatite or a fluorine compound.

| | |
|---|---|
| Hydroxyapatite | 7 wt. % |
| Calcium hydrogen phosphate (2H₂O) | 33 wt. % |
| Glycerol | 10 wt. % |
| Sorbitol | 10 wt. % |
| Carboxymethylcellulose | 1 wt. % |
| Sodium laurylsulfate | 2 wt. % |
| Saccharin sodium salt | 0.3 wt. % |
| Flavor | 1 wt. % |
| Pure water | 35.7 wt. % |

The above-mentioned ingredients were mixed and kneaded in the conventional manner to prepare a hydroxyapatite-containing toothpaste.

(3) Composite Toothpaste Tube

The fluorine-containing toothpaste and the hydroxyapatite-containing toothpaste prepared above were placed in a ratio of 1:4 in a double tube vessel illustrated in FIGS. 1 and 2 under the condition that the former is placed in the inner tube and the latter is placed in the space between the inner tube and the outer tube.

(4) Evaluation of Toothpastes

The composite toothpaste product of the invention prepared in (3) above showed excellent results in the increase of whiteness, removal of bacterial plaque, and inhibition of dental caries, which were comparable to the results observed in Example 1.

Possibility in Industrial Use

The composite toothpaste product of the invention show, when it is employed in tooth-brushing, an excellent effect in increase of whiteness, removal of bacterial plaque, and inhibition of dental caries, which is more effective in tooth-brushing using the conventionally (3) Composite Toothpaste Tube The fluorine-containing toothpaste and the hydroxyapatite-containing toothpaste prepared above were placed in a ratio of 1:3 in a double tube vessel illustrated in FIGS. 1 and 2 under the condition that the former was placed in the inner tube and the latter was placed in the space between the inner tube and the outer tube.

(4) Evaluation of Toothpastes

The composite toothpaste product of the invention prepared in (3) above showed excellent results in the increase of whiteness, removal of bacterial plaque, and inhibition of dental caries, which were comparable to the results observed in Example 1.

EXAMPLE 3

(1) Toothpaste containing Fluorine Compound as Active Ingredient

| | |
|---|---|
| Light calcium carbonate | 10 wt. % |
| Aluminum hydroxide | 10 wt. % |
| Silicic acid anhydride | 12 wt. % |
| Alumina | 3 wt. % |
| Glycerol | 15 wt. % |
| Sorbitol | 10 wt. % |
| Carboxymethylcellulose | 2 wt. % |
| Sodium laurylsulfate | 2 wt. % |
| Sodium monofluorophosphate | 0.3 wt. % |
| Flavor | 1 wt. % |
| Pure water | 34.7 wt. % |

The above-mentioned ingredients were mixed and kneaded in the conventional manner to prepare a fluorine-containing toothpaste.

(2) Toothpaste Containing Hydroxyapatite as Active Ingredient

What is claimed is:

1. A composite toothpaste product comprising a toothpaste containing a hydroxyapatite as a main active ingredient and another toothpaste containing a fluorine compound as a main active ingredient, which are enclosed with a container but separated from each other by a partition united to the container, under the condition that these toothpastes are separated from each other with no contact when it is out of use, and are squeezed out of the container, when in use, in such a manner that the latter toothpaste is enclosed with the former toothpaste.

2. The composite toothpaste product of claim 1, wherein the container comprises double tubes in which one is an outer flexible tube having one open end and another is an inner flexible tube having one open end, the open end of the inner tube being put back from the position of the open end of the outer tube in the longitudinal direction of the tubes, the toothpaste containing a fluorine compound being placed in the inner tube, and the toothpaste containing a hydroxyapatite being placed in a space formed between the inner tube and the outer tube.

3. The composite toothpaste product of claim 1, wherein the hydroxyapatite is contained in the toothpaste containing an hydroxyapatite in an amount of 1 to 30 weight %, based on the total amount of the toothpaste containing an hydroxyapatite and the toothpaste containing a fluorine compound.

4. The composite toothpaste product of claim 1, wherein the fluorine compound is contained in the toothpaste containing a fluorine compound in an amount of 0.002 to 2.0 weight % in terms of an amount of fluorine ion, based on the total amount of the toothpaste containing an hydroxyapatite and the toothpaste containing a fluorine compound.

5. The composite toothpaste product of claim 1, wherein the fluorine compound is contained in the toothpaste containing a fluorine compound in an amount of 0.001 to 3.0 weight % in terms of an amount of fluorine ion, based on the amount of the hydroxyapatite contained in the toothpaste containing an hydroxyapatite.

* * * * *